United States Patent [19]
Northcutt

[11] 3,936,938
[45] Feb. 10, 1976

[54] ORTHODONTIC SPRING APPLIANCE AND SPRING CLIP THEREFOR

[75] Inventor: Michael E. Northcutt, Mountain View, Calif.

[73] Assignee: Aledyne Corporation, Los Altos, Calif.

[22] Filed: May 17, 1974

[21] Appl. No.: 471,175

[52] U.S. Cl. ............................................. 32/14 A
[51] Int. Cl.² ........................................... A61C 7/00
[58] Field of Search .................................... 32/14 A

[56] References Cited
UNITED STATES PATENTS

| | | | |
|---|---|---|---|
| 3,315,359 | 4/1967 | Moss | 32/14 A |
| 3,593,421 | 7/1971 | Brader | 32/14 A |

Primary Examiner—Robert Peshock
Attorney, Agent, or Firm—Schuyler, Birch, Swindler, McKie & Beckett

[57] ABSTRACT

An orthodontic spring appliance which is readily inserted in the mouth and may be stretched to exert a predetermined force is provided by a coil spring having on at least one end a substantially straight wire having protrusions thereon spaced at predetermined intervals. The wire with protrusions may be readily connected to a spring clip which may be attached to the arch wire or a tooth bracket. The clip has a slot therein which is so designed that it readily accommodates the protrusion but prevents the wire from being pulled out by the tension force of the spring.

17 Claims, 14 Drawing Figures

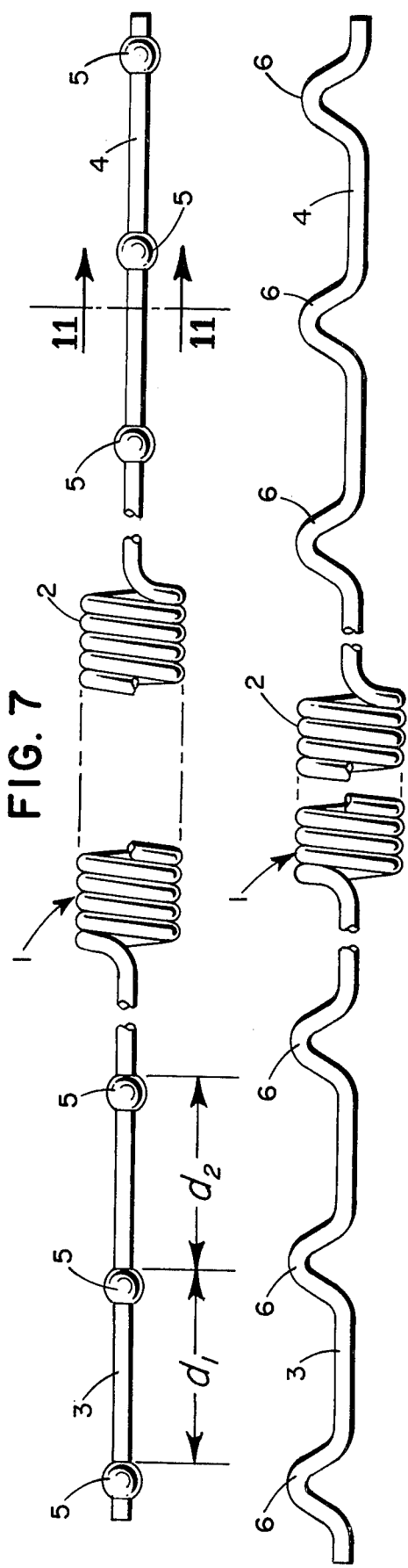
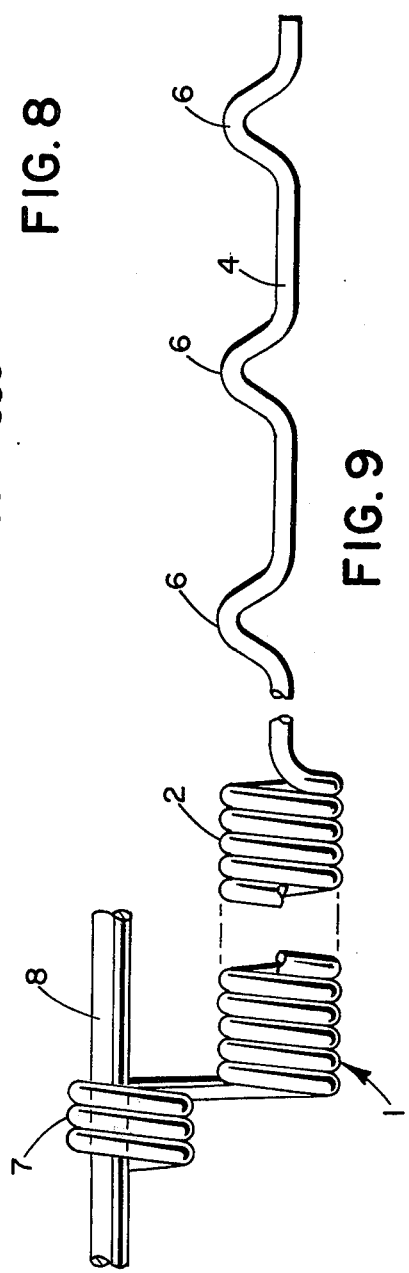
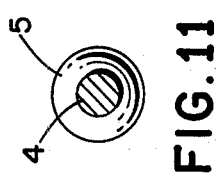
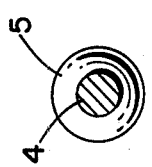

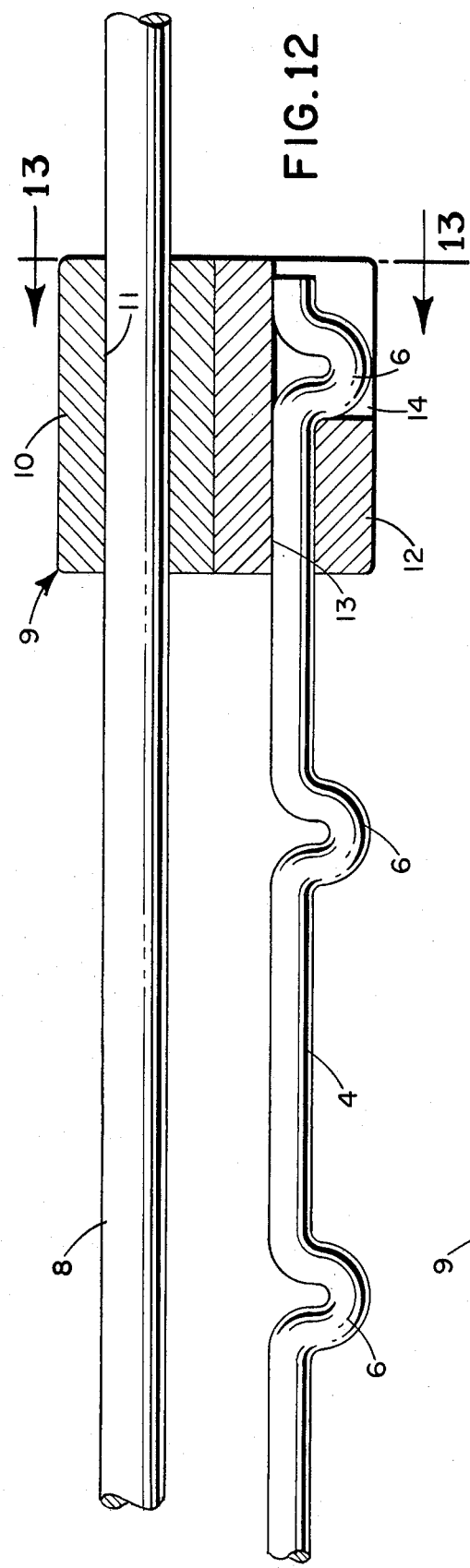
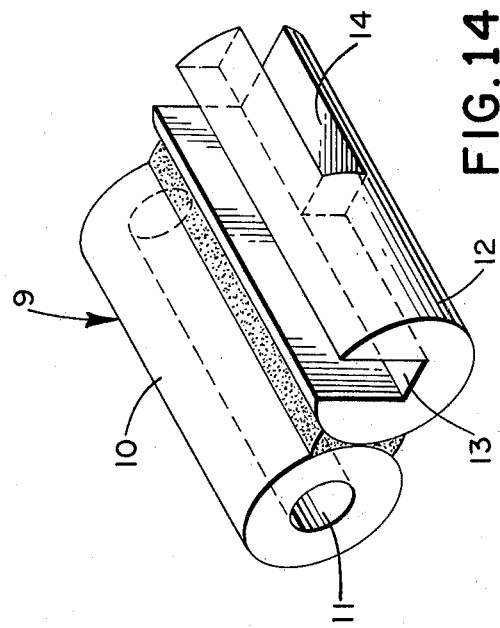
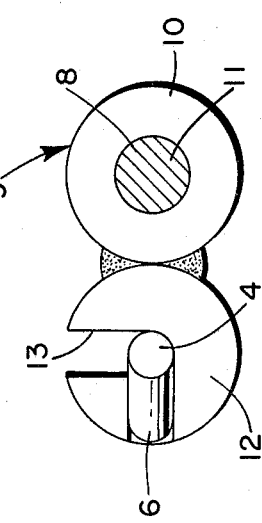

ORTHODONTIC SPRING APPLIANCE AND SPRING CLIP THEREFOR

BACKGROUND OF THE INVENTION

This invention relates to orthodontic appliances and their use in the practice of orthodontics. In particular, this invention relates to coiled wire springs and spring clip retention devices which may be prefabricated and readily installed in the mouth to correct malocclusions of teeth and/or jaws.

Most orthodontists correct maloccluded teeth using a system of arch wires that connect all of the teeth. In approximately 60% of orthodontic cases, protrusive anterior teeth are retracted into non-protrusive position. Retraction is normally effected by a tensile force exerted on the arch wires. These tensile forces have heretofore been created by bending springs into the arch wire itself or by using either elastic rubber bands or metallic coil springs.

Springs built into the arch wire itself are extremely difficult for the orthodontist to fabricate and require considerable non-productive time on the part of the orthodontist. Moreover, they are not readily adapted for use between the upper and lower arches of the teeth and create undesired rotations.

Elastic bands have several advantages insofar as they can be inserted and removed by the patient, do not have to be cleaned since they are disposable and do not have to be reactivated by the orthodontist. However, elastic bands have a number of disadvantages. Elastic bands are easily removed by the patient thereby frustrating the orthodontist's efforts and, furthermore, are subject to interaction with the natural fluids in the patient's mouth. This interaction with fluids in the patient's mouth rapidly reduces the physical properties of the conventional strand elastics resulting in a tensile force reduction of about 40% after the elastics have been in place for several hours. Accordingly, the restoring force exerted by the elastic when stretched to a specific elongation does not remain constant and is difficult to control.

Coiled wire spring appliances have been used in orthodontics and such appliances are discussed in U.S. Pat. No. 3,618,214 to M. M. Armstrong entitled "Coiled Wire Spring Appliances for Use in Orthodontics". However, the devices described therein must be tied at each end which is often a difficult procedure especially in the back of the mouth.

It is an object of this invention to provide a coiled spring device which may be readily inserted in the mouth, easily stretched and readily attached to a spring clip retention device without complicated tying procedures.

It is a further object of this invention to provide a coil spring device which may be readily positioned in the mouth and stretched to a predetermined easily discernable degree of elongation thereby applying a predetermined, readily discernable calibrated tensile force to the arch wires and maloccluded teeth.

It is yet another object of this invention to provide a spring clip retention means to which said coil spring device may be readily attached without complicated tying procedure.

These and other objects of this invention may be achieved by an orthodontic treatment assembly for applying repositioning forces to teeth in a patient's mouth comprising, in combination, means suitable for insertion in the mouth to produce a tension force, said force producing means having a plurality of spaced apart positioning means on at least one end, a spring retention device adapted to engage one of said positioning means and further adapted to be mounted on a stable support.

In a preferred embodiment, the means which produces a tension force comprises a resilient element capable of producing a stable and predictable force upon elongation preferably a metallic coil spring. The coil spring itself preferably has a first end, a central coil section, and a second end. Both of the aforesaid ends are capable of being retained when force is applied thereto and at least one end is a substantially straight wire having a plurality of positioning means spaced at predetermined distances from the central coil. The positioning means may be protrusions on the wire such as nodules, crimps, or peenings. A second retention means adapted to retain said second end may also be provided, the resilient element may be elongated to engage said first and second retention means with at least one of the aforesaid positioning means. The amount of force applied to the resilient element will be proportional to the distance of the engaged positioning means from the central coil section.

Ready retention of an end of the spring which end is a substantially straight wire having protruding means therein can be achieved by a spring retention device comprising means for attachment to a fixed support in the mouth and retention means for retaining an orthodontic spring appliance which retention means comprises an element having means therein constructed and arranged to permit a substantially straight wire shaped end of an orthodontic spring appliance to be readily inserted therein and retained when the spring appliance is under tension. Preferably the spring retention device comprises a tube, capable of being threaded onto an orthodontic arch wire, said tube having attached thereto means for retention of an orthodontic spring appliance which means comprises an element attached to said tube, said element having a slot therein constructed and arranged to permit a substantially straight wire shaped and of the aforesaid metallic coil spring to be inserted therein, said element being further constructed and arranged to retain said wire shaped end therein when said spring appliance is under tension.

A readily applied, easily discernable, calibrated tensile force may be achieved by an orthodontic spring appliance comprising means for producing a force, said means having a plurality of spaced apart positioning means on at least one end. Preferably the orthodontic spring appliance comprises a resilient element which produces a stable and predictable force upon elongation, desirably a metallic coil spring suitable for use in a patient's mouth having a first end, a central coil section and a second end, at least one of said ends being a substantially straight wire having protrusions thereon spaced at predetermined intervals from said central coil section, both of said ends constructed to be retained whereby said spring may be stretched to exert a tensile force.

In this invention, the working forces for the orthodontic device are preferably provided by coil wire springs. When the springs are installed in the mouth, the resulting forces on the maloccluded teeth are determined by the characteristics of the unelongated or static springs, and by the extent of spring elongation.

Selection of wire type and diameter and of coil configuration is important in the manufacture of all embodiments. Spring tempered stainless steel wire stock is currently available having satisfactory strength and elastic properties. Knowing the basic physical properties of a particular wire, the determination of spring parameters such as wire diameter, number of coils and coil diameter is readily made by referring to any of the readily available texts on spring design.

To be functional and comfortable, the coil springs of this invention should have a sufficiently small outside diameter so that they can be accommodated in the limited space available in the vestibules of the mouth. Moreover, the springs should also be available in various length to permit use in a variety of positions and to accommodate the wide ranges of intermaxillary spans in the mouths of different patients. Appliance length is readily determinable because other parameters such as wire diameter, cross-section and material, coil diameter and the number of springs can be varied to provide a spring having the desired unelongated or static length and a desired working elongation.

The invention will be more particularly described with respect to the drawings.

FIG. 7 is an enlarged front view of the orthodontic spring appliance of this invention showing nodular protrusions spaced along the substantially straight wire ends of a coiled spring.

FIG. 8 is an enlarged front view of an alternative embodiment of the spring appliance of this invention wherein the substantially straight wire ends of the spring are crimped to form v-shaped protrusions.

FIG. 9 is an enlarged view of a second alternative, the spring appliance of this invention showing one end having a substantially straight wire with v-shaped protrusions and the other end having a laterally disposed coil extension of the spring through which is threaded an arch wire.

FIG. 10 is an end view of spring of FIG. 9.

FIG. 11 is a sectional view of the substantially straight end of the spring appliance of this invention taken along the line 11—11 of FIG. 7.

FIG. 12 is an enlarged partial sectional view of a second form of the spring retention means of this invention used to connect the spring appliance to an arch wire.

FIG. 13 is a partial sectional view of an orthodontic treatment assembly of this invention taken along the line 13—13 of FIG. 12.

FIG. 14 is a perspective view of a second form of the spring clip retention means of this invention.

Figure 1:
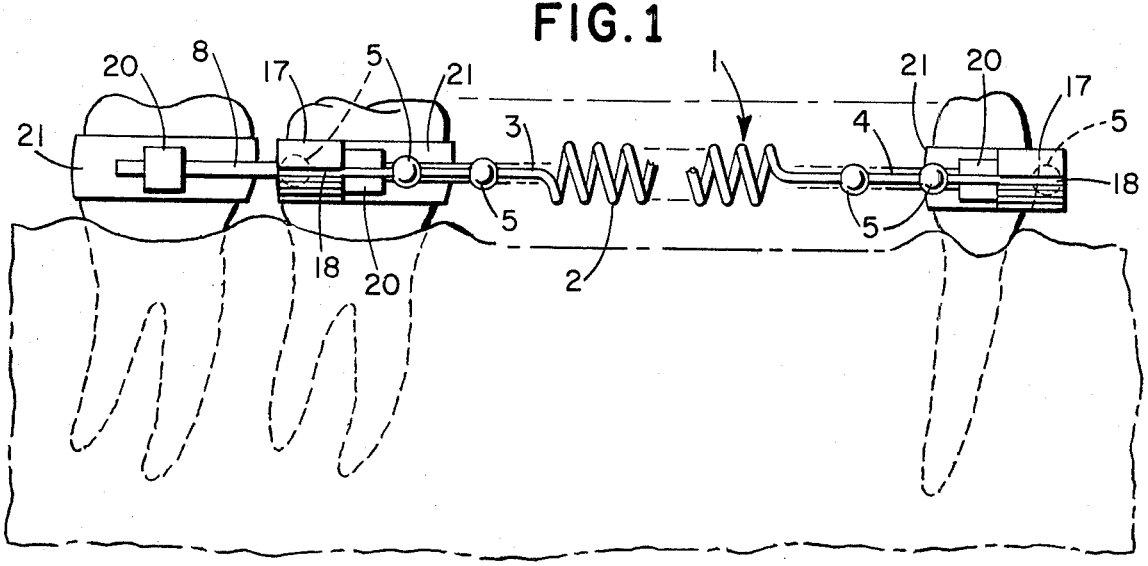
FIG. 1 is a perspective view of the orthodontic treatment assembly of this invention in use to apply forces between two teeth of the dental arch.

As best seen in FIG. 7, spring appliance 1 consists of a central coil portion 2 and substantially straight end wire portions 3 and 4 which have positioning means 5 thereon. The positioning means which are spaced predetermined distances $d_1$, $d_2$, etc., away from central portion 2 of the spring appliance may be either nodules 5, crimps 6 or equivalent devices readily determined by the skilled mechanic. The straight wire end may be peened at regular intervals, however, this method of forming protrusions weakens the wire at the locations peened.

Since one can readily calculate the force required to extend a given spring a given distance, the orthodontist can readily determine the forces applied to the spring by adjusting the position of the nodule or crimp in the spring retention device. The orthodontist need only move the nodule or crimp forward or backward in the spring retention device to vary the amount of force desired.

In another embodiment of this invention shown in FIG. 9, the spring 1 has a substantially straight wire at one end and a tube or loop section 7 at the other end. The loop is designed to be quickly inserted over the end of an orthodontic arch wire 8. The axis of loop 7 is parallel to and laterally disposed from the axis of the coil spring. This arrangement holds the spring away from the gum tissue and away from the biting surface of the teeth. Furthermore, it permits the axis of pull to be kept parallel to the axis of the spring thereby preventing undesirable rotations of the device during use. The loop may simply be a section of the spring itself which may be bent 180° from the horizontal. Alternatively the loop may be a separate device welded or otherwise attached to the side of the spring.

The spring clip retention device 9 as seen in FIGS. 13 and 14 comprises a tube 10 capable of being threaded onto an orthodontic arch wire 8. The central hole 11 of the tube can be either round or square to accommodate the arch wire. A spring retaining element 12 is soldered or otherwise attached to tube 10. A slot 13 is cut into element 12 along the axis of the tube 10. The slot may be partially blocked at one end so that when the protrusions 5 and 6 of spring 1 are inserted into the slot 13, they are captured by the partially blocked end thereby applying a tensile force to the spring 1. In a preferred embodiment, the element 12 has a second slot 14 positioned 90° from the first so that the end of the spring may be inserted in slot 13, twisted and retained by slot 14.

Figure 3:
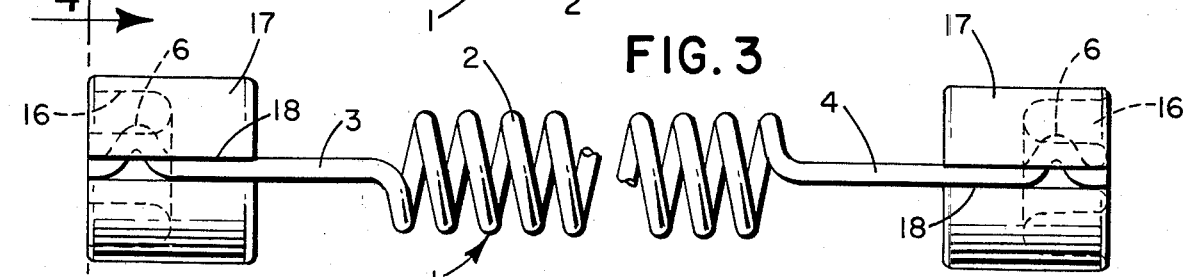
FIG. 3 is a partial perspective view showing a second form of the spring appliance of this invention in stretched position between two spring retention clips.
Figure 4:
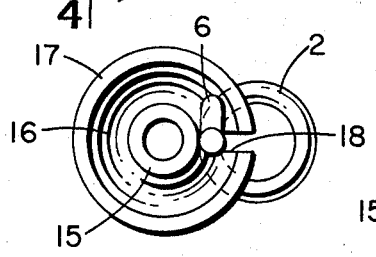
FIG. 4 is an end view of the orthodontic treatment assembly of this invention taken along the line 4—4 of FIG. 3.
Figure 5:
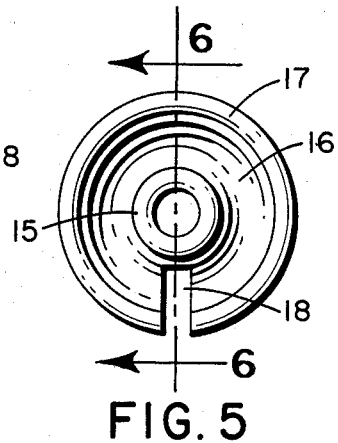
FIG. 5 is a side view of one form of the spring retention clip of this invention.
Figure 6:
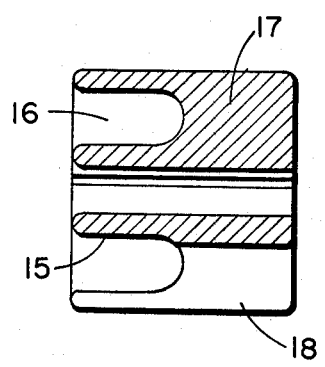
FIG. 6 is a front sectional view of the spring retention clip of this invention taken along the line 6—6 of FIG. 5.

As shown in FIGS. 3 and 6, an alternative form 19 of the spring retention device comprises a spring retaining element integral with and co-extensive with a first tube 15 designed to be threaded or otherwise placed onto the arch wire. In that case a circular groove 16 may be cut out of one end of spring retaining element 17 to permit the protrusion to be caught therein. The groove need not be completely circular and may be any shape so long as it is capable of retaining a protrusion. Preferably, the groove is narrow enough to prevent rotation of the wire end within the groove. A slot 18 permits insertion of the straight end of the spring in element 17.

The spring retention device 9 may be fabricated of relatively soft material and be slotted so that it may be readily inserted over the arch wire and crimped. Alternatively, one end of the spring retention device may be heat treated so that it may be bent or crimped to different lengths. It is preferred, however, that the material is not soft since once crimped the spring retention clip would be unusable.

Figure 2:
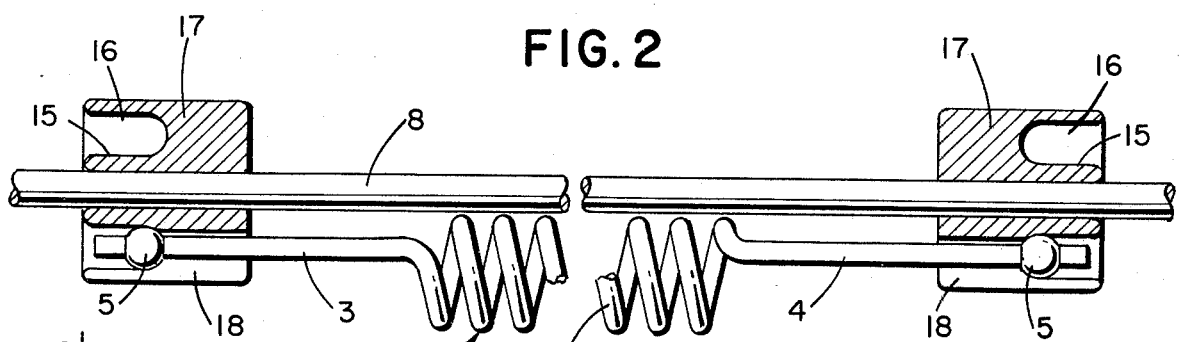
FIG. 2 is a partial sectional view of the orthodontic treatment assembly of this invention showing one form of the spring appliance of this invention held to an arch wire by two spring retention clips shown in section.

As shown in FIGS. 1, 2 and 3, the spring appliance 1 is stretched and retained in spring clip retention device 19 by inserting nodules 5 or crimps 6 in slot 18 of device 19 where they are trapped by groove 16. Upon insertion of the nodules, the device is pulled against and retained by brackets 10 mounted on bands 21.

In actual use, the springs may be applied within one arch as from tooth to tooth as seen in FIG. 1 or alternatively may be applied between arches as from lower molar to upper cuspid for the retraction of upper anterior teeth. A crimp may be placed in the arch wire to prevent lateral movement of the spring retention device. It is not necessary to use a spring retention element to retain the straight end of the springs since one can tie the free end to the brackets disclosed in U.S. Pat. No. 3,775,850.

The disclosures and the descriptions herein are purely illustrative and are not intended to be in any sense limiting. Since variations of the invention will be apparent to those skilled in the art, it is intended that those skilled in the art be limited only by the scope of the appended claims.

I claim:

1. An orthodontic treatment assembly for applying repositioning forces to teeth in a patient's mouth comprising, in combination, means suitable for insertion in the mouth to produce a tension force, said tension producing means comprising a resilient element that produces a stable and predictable force upon elongation of said element, said resilient element having a first end and a second end opposite to said first end, wherein both of said ends are capable of being retained when force is applied thereto, at least one of said ends comprising a force determining element consisting essentially of a substantially straight wire having a plurality of positioning elements thereon, said positioning elements being located on said substantially straight wire at predetermined intervals spaced from each other whereby the amount of elongation of said tension producing means and the force generated thereby is dependent upon which of said positioning elements is inserted in and retained by a retention device, and means for retaining both ends of said resilient element, at least one of said retaining means comprising a retention device, said retention device adapted to be mounted on a stable support and having a slot therein constructed and arranged to permit a substantially straight wire shaped end of said force determining element to be inserted therein and constructed and arranged to retain said straight wire shaped end therein when said resilient element is under tension by retaining said positioning element.

2. The orthodontic treatment assembly of claim 1 wherein said stable support in an arch wire.

3. The orthodontic treatment assembly of claim 1 wherein said resilient element is a metallic coil spring having at least one end which is a substantially straight wire.

4. The orthodontic treatment assembly of claim 3 wherein said retention device comprises a first tube capable of being threaded onto an orthodontic arch wire and having an element attached thereto having a slot therein parallel to and laterally disposed from the axis of said tube.

5. The orthodontic treatment assembly of claim 4 wherein said element comprises a second tube co-axial and integral with said first tube, said retention device being cylindrical shape, flat at one end and having a substantially circular groove at its opposite end, said groove being co-axial with said tube.

6. The orthodontic treatment assembly of claim 4 wherein said metallic coil spring comprises a central coil section, a first end and a second end opposite to said first end, both of said ends so constructed and arranged that they may be retained when force is applied thereto, thereby placing said resilient element under tension, at least said first end consisting essentially of a substantially straight wire having a plurality of positioning elements thereon spaced at predetermined intervals from said central coil section, said assembly further including a second retention device adapted to retain said second end whereby said coil spring may be elongated to engage said first and second retention devices, the amount of force applied to said coil spring being proportional to the distance of the positioning elements engaged from said central coil section.

7. The orthodontic treatment assembly of claim 6 wherein both said first end and said second end consist essentially of a substantially straight wire having positioning elements thereon spaced at predetermined intervals from said central coil section.

8. The orthodontic treatment assembly of claim 7 wherein said second retention device is adapted to engage one of the positioning elements of said second end and further adapted to be mounted on a second stable support.

9. The orthodontic treatment assembly of claim 8 wherein said second stable support is an arch wire.

10. The orthodontic treatment assembly of claim 6 wherein said second end attached to said central portion comprises means defining a channel for use on an arch wire, said channel being parallel to and laterally disposed from the central axis of said coil spring.

11. A spring retention device for orthodontic spring appliances comprising means for attachment to a fixed support in the mouth and means for retaining an orthodontic spring appliance comprising an element attached to said means for attachment, said element having a slot therein constructed and arranged to permit a substantially straight wire shaped end of an orthodontic spring appliance having a plurality of positioning elements to be inserted therein and constructed and arranged to retain said straight wire shaped end therein when said spring appliance is under tension by retaining said positioning element.

12. The spring retention device of claim 11 wherein said means for attachment to a fixed support is a first tube capable of being threaded onto an orthodontic arch wire said means for retaining an orthodontic spring appliance comprises an element attached to said tube, said element having a slot therein constructed and arranged to permit a substantially straight wire shaped end of said orthodontic spring to be inserted therein and constructed and arranged to retain said wire shaped end therein when said spring appliance is under tension.

13. The spring retention device of claim 12 wherein said element comprises a second tube, the axis of which is parallel to the axis of said first tube.

14. The spring retention device of claim 12 wherein said second tube is co-axial with and larger in diameter than said first tube.

15. The spring retention device of claim 14 wherein said slot is elongated and parallel to the axis of said first tube, said means being flat at one end and having a substantially circular groove at said other end, said groove being co-axial with said first tube.

16. The spring retention device of claim 13 wherein said element is parallel to the axis of said tube and the cross-sectional area of one end of said slot is less than the cross-sectional area of the other end.

17. The spring retention device of claim 16 wherein the longitudinal axis of said element is laterally disposed from the longitudinal axis of said tube.

* * * * *